United States Patent
Brandelik et al.

(10) Patent No.: US 6,313,645 B1
(45) Date of Patent: Nov. 6, 2001

(54) METHOD OF DETERMINING THE VOLUMETRIC PROPORTION OF LIQUID WATER AND THE DENSITY OF SNOW AND A DEVICE FOR CARRYING OUT THE METHOD

(75) Inventors: Alexander Brandelik, Karlsruhe; Christof Hübner, Edingen-Neckarhausen, both of (DE)

(73) Assignee: Forschungszenfrum Karlsruhe GmbH, Karlsruhe (DE)

( * ) Notice: Subject to any disclaimer, the term of this patent is extended or adjusted under 35 U.S.C. 154(b) by 0 days.

(21) Appl. No.: 09/568,080

(22) Filed: May 10, 2000

Related U.S. Application Data

(63) Continuation-in-part of application No. PCT/EP98/07190, filed on Nov. 11, 1998.

(30) Foreign Application Priority Data

Dec. 11, 1997 (DE) .............................................. 197 55 052

(51) Int. Cl.⁷ ........................ G01R 27/26; G01R 27/32; G01N 25/62; G01W 1/00; G01F 23/00
(52) U.S. Cl. ........................ 324/664; 324/670; 324/643; 73/73; 73/170.26; 73/304 C; 73/861.43
(58) Field of Search ................................ 324/670, 643, 324/664; 73/170.26, 861.42, 73, 304 C; 250/253

(56) References Cited

U.S. PATENT DOCUMENTS

| | | | |
|---|---|---|---|
| 2,817,234 | * 12/1957 | Campbell | 73/304 R |
| 3,240,054 | * 3/1966 | Roth | 340/582 |
| 3,475,960 | * 11/1969 | Miller | 73/304 R |
| 3,986,110 | * 10/1976 | Overall et al. | 73/304 C |
| 4,389,900 | 6/1983 | Guiterrez | 73/861.42 |
| 4,766,369 | 8/1988 | Weinstein | 324/670 |
| 5,191,791 | * 3/1993 | Gerardi et al. | 73/178 R |
| 5,398,547 | 3/1995 | Gerardi et al. | 73/170.26 |

FOREIGN PATENT DOCUMENTS

| | | |
|---|---|---|
| 0 091 522 | 6/1982 | (EP) . |
| 2 326 703 | 4/1977 | (FR) . |
| 58 018156 | 2/1983 | (JP) . |
| WO 96/22522 | 7/1996 | (WO) . |

OTHER PUBLICATIONS

Sihvola et al. , Effective Premittivity of Dielectric Mixtures, Jul. 1988, IEEE vol. 26, No. 26.*
A. Denoth, The Monopole–Antenna, Sep. 1997, EEE vol. 35, No. 5.*
Sihvola et al. , Snow Fork for Field Determination of the Density and wetness profile of a Snow Pack, Sep. 1986, IEEE vol. GE–24, No. 5.*

* cited by examiner

*Primary Examiner*—Glenn W. Brown
*Assistant Examiner*—Wasseem H. Hamdan
(74) *Attorney, Agent, or Firm*—Klaus J. Bach

(57) ABSTRACT

In a method and apparatus for determining the volumetric proportion of water in snow and the density of snow, a probe consisting of at least three parallel, but differently spaced, electrical conductors is installed in an area so that the probe is surrounded by the snow, an electromagnetic signal is applied repeatedly to pairs of the conductors for determining different dielectricity coefficients, wherefrom the actual dielectricity coefficient is calculated based on probe-specific calibration data and the measuring steps are repeated with a different frequency for which the dielectricity coefficients of the water and ice are known and the volumetric parts of the snow, that is of the water, ice and air in the snow cover is calculated using the law of mass conservation.

8 Claims, 2 Drawing Sheets

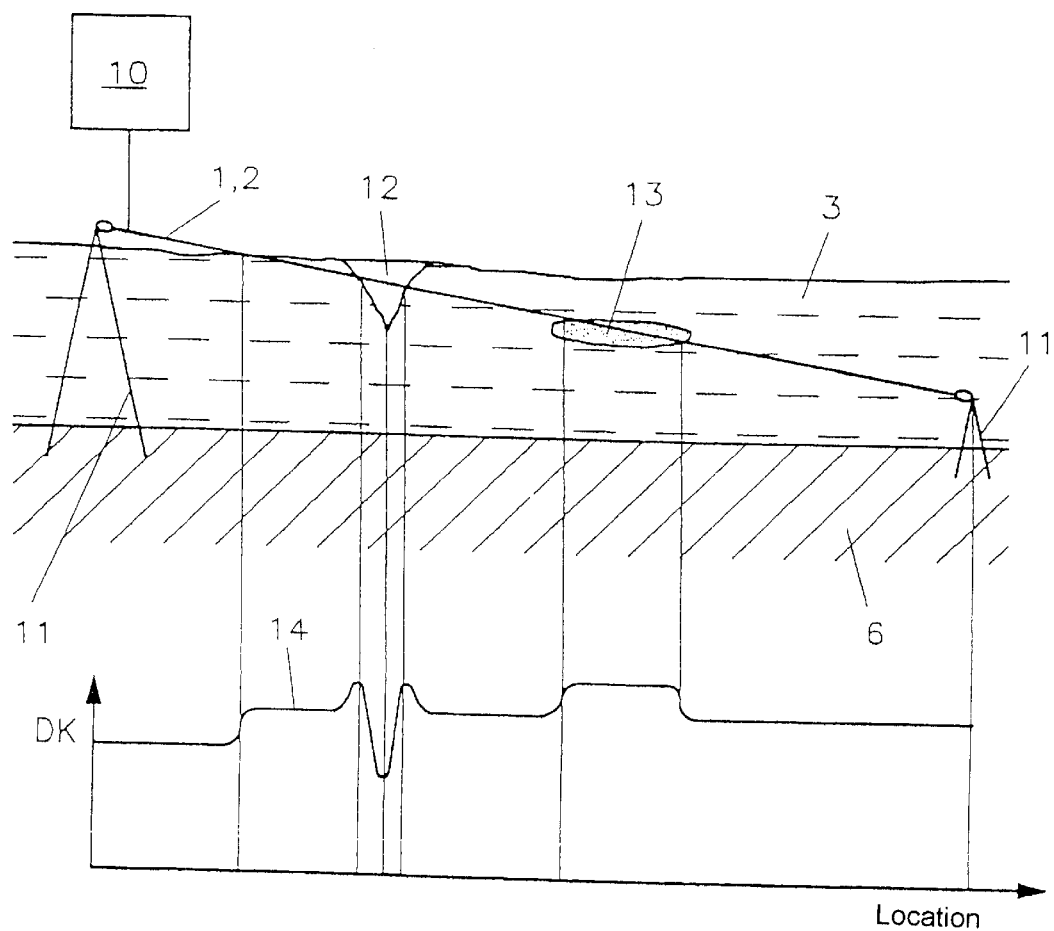

METHOD OF DETERMINING THE VOLUMETRIC PROPORTION OF LIQUID WATER AND THE DENSITY OF SNOW AND A DEVICE FOR CARRYING OUT THE METHOD

This is a continuation-in-part application of international application PCT/EP98/07190 filed Nov. 11, 1998 and claiming the priority of German patent application 197 55 052.5 filed Nov. 12, 1997.

BACKGROUND OF THE INVENTION

The invention relates to a method for determining the volumetric proportion of liquid water and the density of snow and to a device for carrying out the method.

The determination and the effects of the global climatic changes with regard to ice and snow requires the measurement of the snow conditions, particularly its density and the liquid water content thereof.

These are also the most important values for issuing avalanche and flood warnings.

The expected filling degrees of reservoirs of northern hydro-electric generating stations must also be predicted far in advance using these parameters.

M. Schneebeli et al., of the Eidg. Institut für Schnee and Lawinenforschung SLF, Davos/Switzerland, and Meteo France, St. Martin d' Heres/France, report a possible solution in the publication "Measurement of Density and Wetness in Snow Using Time-Domain-Reflectometry" in print by the publication Am. Glacial, 26, 1997. The article also describes other solutions with short critical comments. Their solution is based on calibration in a laboratory. They were only able to determine the density of dry snow in a sufficiently good way. It is pointed out that, for the determination of two unknowns (density and moisture), at least two independent information sources (linearly independent measurement results) are required. Since snow is a three-component mixture, three sources are required wherein the third source is provided by the law of mass conservation. The above authors have utilized only one source. Therefore, measurements in moist snow had to fail as reported by them.

The report by Sihvola, A. and Tiuri, M. 1986, Snow fork for field determination of the density and wetness profiles of a snow pack, IEEE Trans. Geosci. Remote Sens. GE 24(5), 717–721, describes a snow fork. This apparatus measures at about 1 GHz the complex (that is, two sources) dielectricity coefficients, wherein at the same time the density and moisture content of the snow is determined. However, a continuous measuring operation of this apparatus was not reported. Because the imaginary part of the DK is extremely small at these frequencies, the measurements are highly uncertain particularly if the snow is contaminated. Furthermore, the apparatus measures only over a very small space.

Another solution by A. Denoth: The monopole antenna: A practical Snow and Soil Wetness Sensor, in IEEE: Transactions on Geoscience and Remote Sensing. Vol. 35, No. 5, September 1997 interconnects the KD-value with the density if the snow is dry (on the basis of empirical knowledge). The density change over time is extrapolated for a later time and is then taken as a given value.

With the density and the measured KD value of the moist snow mixture, the moisture content is then determined. This procedure is inaccurate since the extrapolation presumes a certain snow development. If, however, in the mean time, there was a snow melt or re-freezing, that presumption is incorrect. The method fails completely if the time during with the snow is dry is too short, or if the falling snow is already moist.

None of the known apparatuses can eliminate the falsifying effects of the gap between the snow and the instrument, which is always present. Also for this reason, there is no apparatus with an expansive or large measuring area. No apparatus could indicate local inhomogeneities along a path or over an area.

It is the object of the invention to provide a method of the type described above in such a way that disturbances by the measuring system itself are not possible and an apparatus for carrying out the method.

SUMMARY OF THE INVENTION

In a method and apparatus for determining the volumetric proportion of water in snow and the density of snow, a probe consisting of at least three parallel, but differently spaced, electrical conductors is installed in an area so that the probe is surrounded by the snow, an electromagnetic signal is applied repeatedly to pairs of the conductors for determining different dielectricity coefficients, wherefrom the actual dielectricity coefficient is calculated based on probe-specific calibration data and the measuring steps are repeated with a different frequency for which the dielectricity coefficients of the water and ice are known and the volumetric parts of the snow that is of the water, ice and air in the snow cover is calculated using the law of mass conservation.

In the method according to the invention, it is novel and advantageous that the full information is obtained by the same apparatus and at the same time, that is, simply by a frequency switchover, that measurements are taking place free of destructive influences and with disregard of the effect of any gap formed between the conductors and the surrounding snow, that data are obtained over a relatively large path length or over a relatively large area, that such an apparatus may be in operation over a long period (months) and that local inhomogeneities are qualitatively indicated.

Below, the invention will be described in greater detail on the basis of examples with reference to the figures:

BRIEF DESCRIPTION OF THE DRAWINGS

FIG. 3 shows an exemplary location dependent DK curve for several typical inhomogeneities in the snow.

DESCRIPTION OF PREFERRED EMBODIMENTS

Figure 1:
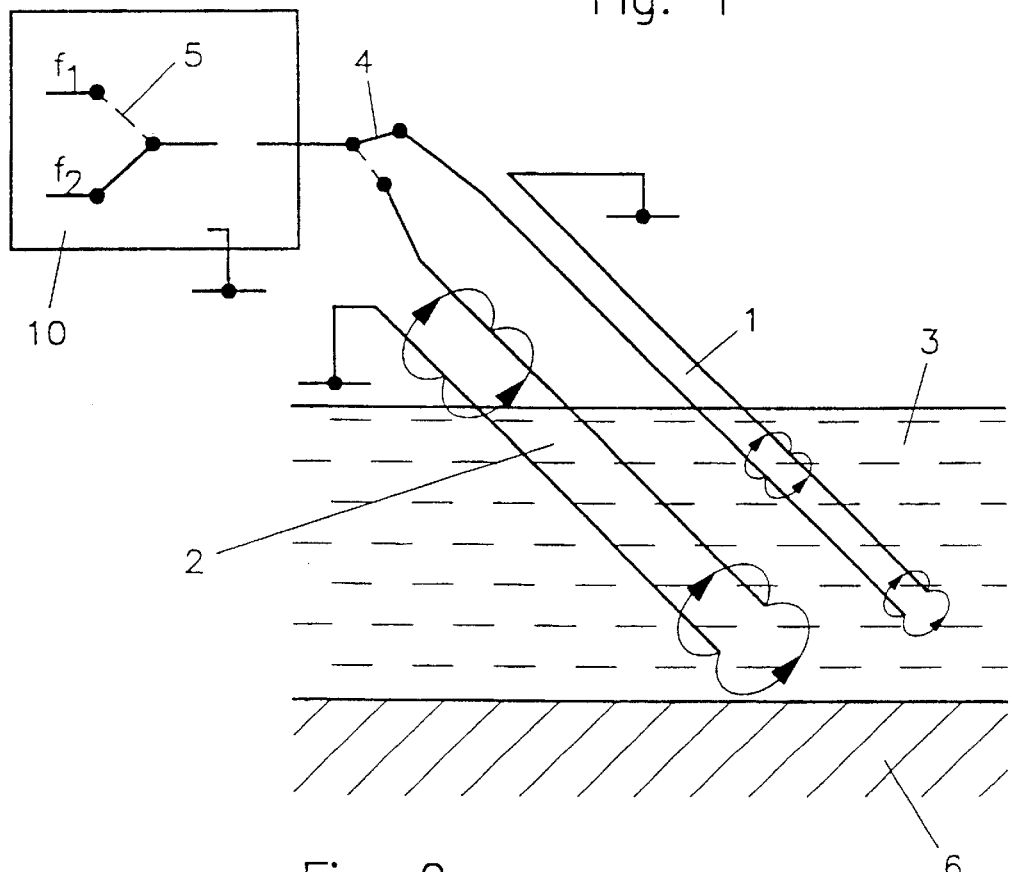
FIG. 1 shows a schematic representation of a multi-vein probe in snow.

An extensive concurrent measurement, which is obtained by the same apparatus and therefore is inherent, supplies the density and the moisture content.

The dielectricity coefficient DK of the snow is measured along a long unshielded cable pair enclosed in the snow in at least two frequency ranges wherein the cable is installed before the snowfall. The first range is selected to be above the relaxation dispersion of the ice DK. The second range is determined to be within the dispersion range or below.

Important is that there is a clear DK difference of ice between the two ranges.

The snow is a mixture of ice E, water W and air L. Their volumetric proportions represent the unitary measuring volumes E+W+L=1 (law of mass conservation).

Of the three information sources, that is, the two DK measurements and the law of mass conservation, the three unknown E, W and L are determined. From these numbers, the density D, D=(E*ice density+W*water density)/(E+W+L), wherein W is the desired moisture content.

Further advantageous features:

Between the snow and the measuring instrument, there is always a certain gap. This gap, which highly falsifies the DK measurements grows even further if the measurements occur over an extended period. In order to obtain the real, non-falsified value of the snow-DK, at least two cable pairs are utilized which generate magnetic fields of different penetration depths. Before the cables are placed in service their sensitivities in different dielectric media are determined by laboratory measurements or by field calculations. With two measurements with these two cables for different penetration depths of the electric field, the real DK and the width of the gap are determined since, with a small penetration depth, the influence of the gap on the DK is greater. We have combined the two pairs of cables into a single three-wire cable. In this way, a sensor is formed and good conditions are provided for the inherent measurement. As a result, a measuring station can be kept in operation for an extended period (winter period) with good measurement accuracy inspite of an increasing gap width.

The values D and W were formed as average values along a long cable. The longer the cable, the more representative is the measured value for a relatively large area. With the usual measuring instruments, only lengths of 40 to 60 m can be covered.

If the snow-DK was measured by the use of TDR (Time-Domain-Reflectometer), a qualitative representation of the local DK change along the measurement cable is possible. This distribution provides for additional, very important information about the homogeneity of the snow along the cable.

Ice lenses, ice boards, percolation paths can be represented in this way and can be included in the avalanche and flood warnings. To this end, the calculation algorithms of the inverse reconstruction of cable parameters, which have been made known in the literature, are utilized.

The measuring cable can be laid out along various paths. We propose an arrangement, for example, with a small angle with respect to the ground surface. In this way, horizontal as well as vertical distributions can be approximated. With several cables arranged cross-wise area-like representations can be approximated. This is desirable particularly for the calibration of remotely acquired data.

FIG. 1 shows two conductor pairs 1, 2, which extend partially in a snow cover 3 above the ground 6. Instead of the four conductors, a three-wire cable can be used, wherein the individual conductors are spaced differently. The penetration depth of the measurement field is determined by the conductor distances of two respective conductors. The distances between the conductors 1, 2 are optimally selected so that the difference of the penetration depths of the two pairs of conductors is comparable with the width of the expected air gaps. Experience shows that the air gap is between about 0.5 and 3 mm. With a change-over switch 4, the conductor pairs 1, 2 can be alternatively switched on. The DK-measuring apparatus 10 can operate on at least two frequencies 5. At the conductors 1, 2, field lines are indicated which represent the different penetration depths of the field.

Figure 2:
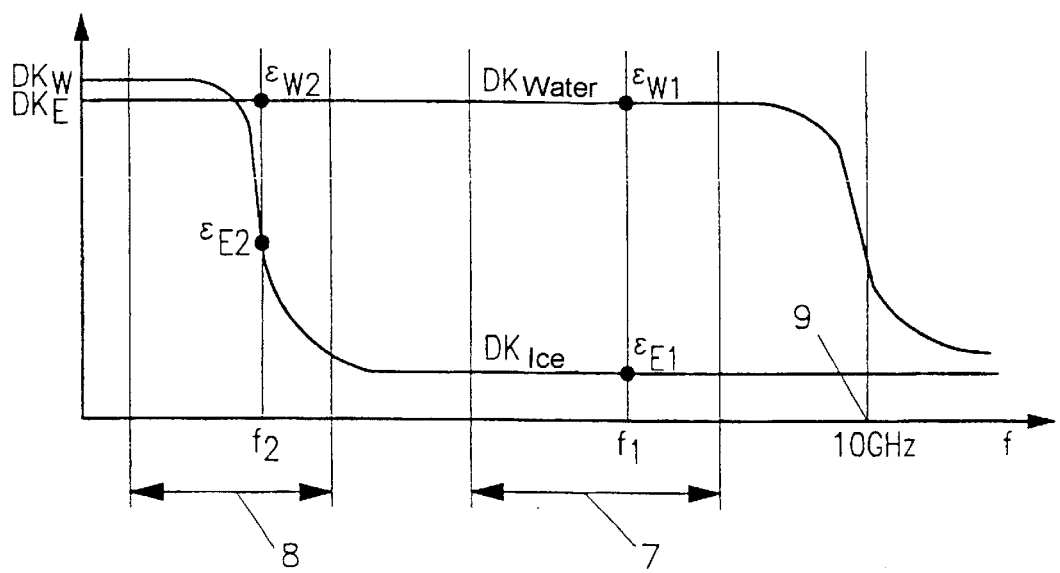
FIG. 2 shows the frequency-dependent DK curve of water and ice dependent on the measuring frequency.

FIG. 2 shows which frequency ranges f1 and f2 are selected for the two measuring ranges. It is generally sufficient if the DK of ice or water are different for one of the two frequencies. With frequencies, which are higher than several GHz, no measurements should be made since, then the penetration depth of the measuring field is too small. This reduces the sensitivity. It is recommended to use a frequency f1 at which the DK of water is at a maximum and that of ice is at a minimum (measuring range) and a frequency of f2 in the area of the switch-back point of the ice-DK curve (measuring range 8).

FIG. 3 shows conductors 1, 2, which extend between anchors 11 at an inclined angle. The conductors 1, 2 extend partially in air and partially within the snow cover 3. In the lower part of the figure, the DK curve 14 with localized resolution of the sensor is represented. The inhomogeneities in the snow cover 3 and also the transition air-snow, the percolation funnel 12 and the ice lens 13 can be clearly recognized.

What is claimed is:

1. A method for determining the volumetric proportion of liquid water and the density of snow, including the following method steps:

a) installing a probe consisting of at least three electrical conductors which are disposed parallel to, and at different distances from, one another before a snow fall or in an established snow cover, b) applying to two of the conductors an electromagnetic signal with a frequency of which the dielectricity coefficient of the water and the ice are known and determining the dielectricity coefficient of the snow, with an unavoidable air gap around the probe, from the transmission behavior of the electromagnetic signal, c) repeating the determination of the dielectricity coefficient wherein the penetration depth of the measuring field of the probe is different from the first measurement by selecting a different conductor spacing, d) calculating from the two measurements the real dielectricity coefficient, which is not influenced by the gap, by using probe-specific calibration data, e) repeating the method steps b), c), and d) with another measuring frequency for which the dielectricity coefficient of the water and the ice is known, but of which at least one has a value different from before, and f) calculating the volumetric parts of the snow that is of the water, ice and air from the real dielectricity coefficient using the law of mass conservation.

2. A method according to claim 1, wherein time range reflectometry is used for the determination of the dielectricity coefficient of the snow, whereby the local inhomogeneities along the probe are calculated by the method of reconstruction of conductor parameters and, as a result, the location of ice lenses, ice boards, and percolation locations are determined.

3. A method according to claim 1, wherein electric conductors are utilized which extend partially normal or at an angle to the surface whereby the snow height is determined from a reflection picture.

4. A method according to claim 1, wherein the electrical conductors are arranged cross-wise, in an area-surrounding manner or snake-like so as to approximate an area determination.

5. An apparatus for determining the liquid content and the density of snow by dielectric measurements, comprising:

a) a measuring electrode arrangement consisting of a probe having at least three electrical conductors, which are disposed in parallel with one another and at different distances and surrounded by snow, wherein the conductors of said probe comprises a flexible in shielded flat cable with insulation, b) a dielectricity measuring device having at least two measuring frequencies wherein the probe is electrically connected to the dielectricity measuring device wherein the dielectricity measuring device is a time range reflectometer whose signal travel time is connected to the dielectricity coefficient by the capacitive probe parameters, and c) a switch-over element for the connection of various pairs of conductors for adjusting the penetration depth.

6. An apparatus according to claim 5, wherein said flat cable is a three-conductor cable.

7. An apparatus according to claim 5, wherein said probe extends between anchoring locations.

8. An apparatus according to claim 5, wherein an extended length probe is provided which is disposed at an angle with respect to the ground surface in such a way that one end of the probe is higher than the expected snow level.

* * * * *